US012679840B2

(12) United States Patent
Chen et al.

(10) Patent No.: US 12,679,840 B2
(45) Date of Patent: Jul. 14, 2026

(54) PROCESS FOR THE PREPARATION OF (9S)-N-[3-(6-METHYLPYRIMIDIN-4-YL)-3-AZABICYCLO[3.2.1]OCTAN-8-YL]-9-(2,3,4-TRIFLUOROPHENYL)-6,7,8,9-TETRAHYDRO-5H-[1,2,4]TRIAZOLO[1,5-A]AZEPIN-2-AMINE AND ITS SOLID FORM

(71) Applicant: Hoffmann-La Roche Inc., Little Falls, NJ (US)

(72) Inventors: Weichun Chen, Shanghai (CN); Guocai Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 488 days.

(21) Appl. No.: 18/331,792

(22) Filed: Jun. 8, 2023

(65) Prior Publication Data

US 2024/0018143 A1 Jan. 18, 2024

Related U.S. Application Data

(63) Continuation of application No. PCT/EP2021/084887, filed on Dec. 9, 2021.

(30) Foreign Application Priority Data

Dec. 11, 2020 (WO) ................ PCT/CN2020/135740

(51) Int. Cl.
*C07D 471/08* (2006.01)

(52) U.S. Cl.
CPC ........ *C07D 471/08* (2013.01); *C07B 2200/13* (2013.01)

(58) Field of Classification Search
CPC ... A61P 25/28; C07B 2200/13; C07D 471/08; C07D 487/04; A61K 31/55
See application file for complete search history.

(56) References Cited

FOREIGN PATENT DOCUMENTS

| | | |
|---|---|---|
| WO | 2011/086098 A1 | 7/2011 |
| WO | 2018/011164 A1 | 1/2018 |

(Continued)

OTHER PUBLICATIONS

Hilfiker et al., Relevance of Solid-state Properties for Pharmaceutical Products, Polymorphism in the Pharmaceutical Industry, Chapter 1, WILEY-VCH Verlag GmbH & Co. KGaA, 2006 (Year: 2006).*

"International Preliminary Report on Patentability—PCT/EP2021/084887" (Report Issuance Date: Jun. 13, 2023; Chapter I),:pp. 1-10 (Jun. 22, 2023).

"International Search Report—PCT/EP2021/084887" (w/Written Opinion),:pp. 1-18 (Mar. 22, 2022).

(Continued)

*Primary Examiner* — Kortney L. Klinkel
*Assistant Examiner* — Padmaja S Rao
(74) *Attorney, Agent, or Firm* — Cindy S. Shu

(57) ABSTRACT

The present invention relates to a process for the preparation of a compound (I), (I)

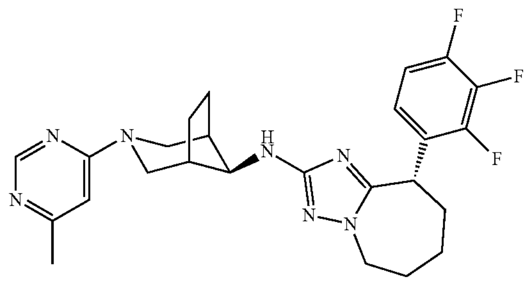

and its solid form, which is a modulator of γ-secretase and may be useful for prophylaxis and treatment of a disease associated with the deposition of β-amyloid in the brain, in particular Alzheimer's disease, and other diseases such as (Continued)

Process for the preparation of rac-(9S)-N-[3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and its solid form cerebral amyloid angiopathy, hereditary cerebral hemorrhage with amyloidosis, Dutch-type (HCHWA-D), multi-infarct dementia, dementia pugilistica and Down syndrome.

18 Claims, 2 Drawing Sheets

(56) References Cited

FOREIGN PATENT DOCUMENTS

| | | | |
|---|---|---|---|
| WO | 2018/060300 | A1 | 4/2018 |
| WO | 2018/083050 | A1 | 5/2018 |
| WO | 2019/141832 | A1 | 7/2019 |
| WO | 2020/136188 | A1 | 7/2020 |
| WO | 2021/105337 | A1 | 6/2021 |

OTHER PUBLICATIONS

Ratni, H., et al., "Discovery of RO7185876, a Highly Potent γ-Secretase Modulator (GSM) as a Potential Treatment for Alzheimer's Disease" ACS Med Chem Lett 11(6):1257-1268 (Jun. 11, 2020).

Ratni, H., et al., "Discovery of RO7185876, a Highly Potent γ-Secretase Modulator (GSM) as a Potential Treatment for Alzheimer's Disease" ACS Med Chem Lett (Supporting Information), 11(6):1-13 (Jun. 11, 2020).

Edited by Noriaki Hirayama, "Producing Crystals of Organic Compounds Handbook—Principles and Know-how-, Maruzen Co., Ltd." (with English translation), 57-84 (2008).

Teruzo Asabara, Solvents Handbook, Kodansha Co., Ltd. (with English translation), (1985).

* cited by examiner

Process for the preparation of rac-(9S)-N-[3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and its solid form

PROCESS FOR THE PREPARATION OF (9S)-N-[3-(6-METHYLPYRIMIDIN-4-YL)-3-AZABICYCLO[3.2.1]OCTAN-8-YL]-9-(2,3,4-TRIFLUOROPHENYL)-6,7,8,9-TETRAHYDRO-5H-[1,2,4]TRIAZOLO[1,5-A]AZEPIN-2-AMINE AND ITS SOLID FORM

CROSS-REFERENCE TO RELATED APPLICATIONS

This application is a continuation of International Application No. PCT/EP2021/084887, filed Dec. 9, 2021, which claims benefit of priority to International Application No. PCT/CN2020/135740 filed Dec. 11, 2020, which is incorporated herein by reference in its entirety.

FIELD OF THE INVENTION

The present invention relates to a process for the preparation of a compound (I)

(I)

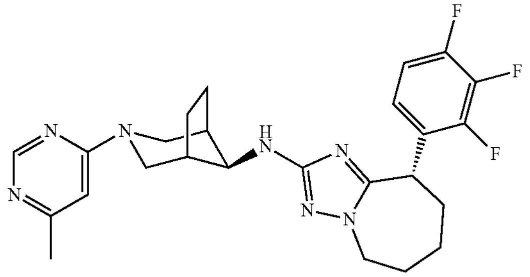

and solid form of compound (I), which is a modulator of γ-secretase and may be useful for prophylaxis and treatment of a disease associated with the deposition of 0-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

BACKGROUND OF THE INVENTION

The synthetic approach of compound (I) was disclosed in WO 2018060300, WO 2019141832, WO2018083050, and WO2011086098. However, the current processes are not suitable for large-scale production due to the following issues:

(a) 3 synthesis steps plus SFC with very low yield (about 13%).

(b) column purification with tedious work up process for

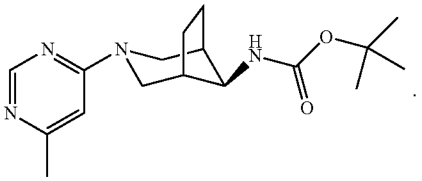

(c) high cost due to racemic synthesis and SFC separation.

(d) safety, repeatability, and scalability concerns for the newly form tri-azole ring during large scale production.

SUMMARY OF THE INVENTION

Based on the issues above, one object of this invention therefore is to find an efficient chiral synthetic approach, which can address some or all of above issues and be applied on a technical scale with much greener condition.

One aspect of the present invention relates to process for the preparation of a compound (I), (I)

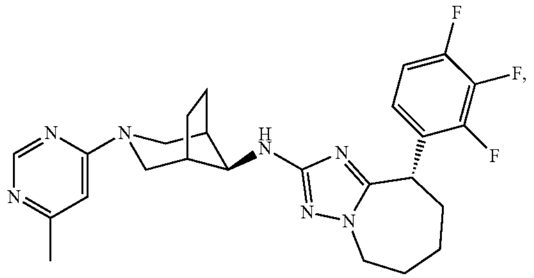

comprising the following steps:

step a) formation of compound (III), (III)

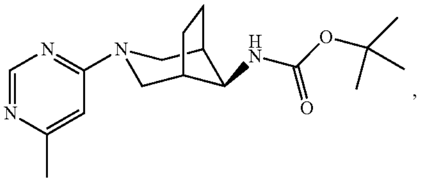

via the reaction of compound (II) (prepared according to the process described in WO2020136188), (II)

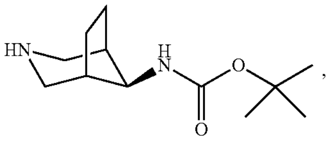

and 4-chloro-6-methyl-pyrimidine;

step b) formation of compound (IV), (IV)

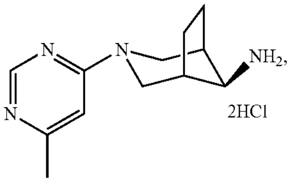

via de-protection reaction of compound (III) and formation of HCl salt;

step c) cross coupling forming of compound (I), (I)

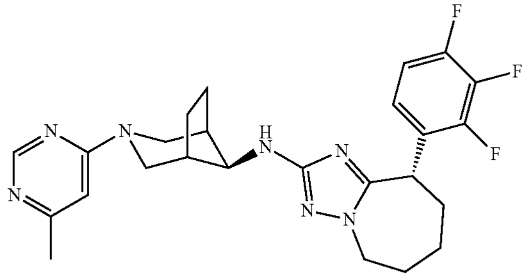

via Buchwald cross coupling reaction from compound (IV) and compound (V) (prepared according to the process described in WO 2019141832), (V)

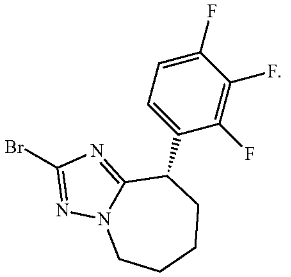

Another aspect of the present invention relates to a solid form of compound (I).

In one embodiment, the solid form of compound (I) is Form A that exhibits an X-ray powder diffraction (XRPD) pattern with characteristic peaks expressed in degrees 2-theta at 15.6°±0.2°, 16.1°±0.2°, 18.4°±0.2°, 19.3°±0.2°, 20.1°±0.2°, and 21.8°±0.2°.

In a further embodiment, the solid form of compound (I) is Form A that exhibits an X-ray powder diffraction (XRPD) pattern with characteristic peaks expressed in degrees 2-theta at 8.9°±0.2°, 10.0°±0.2°, 12.6°±0.2°, 15.6°±0.2°, 16.1°±0.2°, 16.7°±0.2°, 17.9°±0.2°, 18.4°±0.2° 18.7°±0.2° 19.3°±0.2° 20.1°±0.2° 20.8°±0.2° 21.8°±0.2° 22.5°±0.2°, 23.2°±0.2°, 25.3°±0.2°, and 25.4°±0.2°.

In a further embodiment, the solid form of compound (I) is Form A that exhibits an X-ray powder diffraction (XRPD) pattern shown in FIG. 1

In a further embodiment, the solid form of compound (I) is Form A with a differential scanning calorimetry (DSC) thermogram comprising endothermic peak with onset temperature at about 205.5° C.±3° C.

In another embodiment, provided herein is a pharmaceutical composition comprising the solid form disclosed herein; and a pharmaceutically acceptable carrier, excipient, diluent, adjuvant, vehicle or a combination thereof.

In another embodiment, provided herein is a solid form disclosed herein for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome.

In another embodiment, provided herein is the use of a solid form disclosed herein for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome.

In another embodiment, provided herein is the use of the solid form disclosed herein or the pharmaceutical composition for the manufacture of a medicament for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome.

In another embodiment, provided herein is a method for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome, which method comprises administering a therapeutically effective amount of the solid form or the pharmaceutical composition disclosed herein.

DETAILED DESCRIPTION OF THE INVENTION

Abbreviation

ACN Acetonitrile

Figure 1:
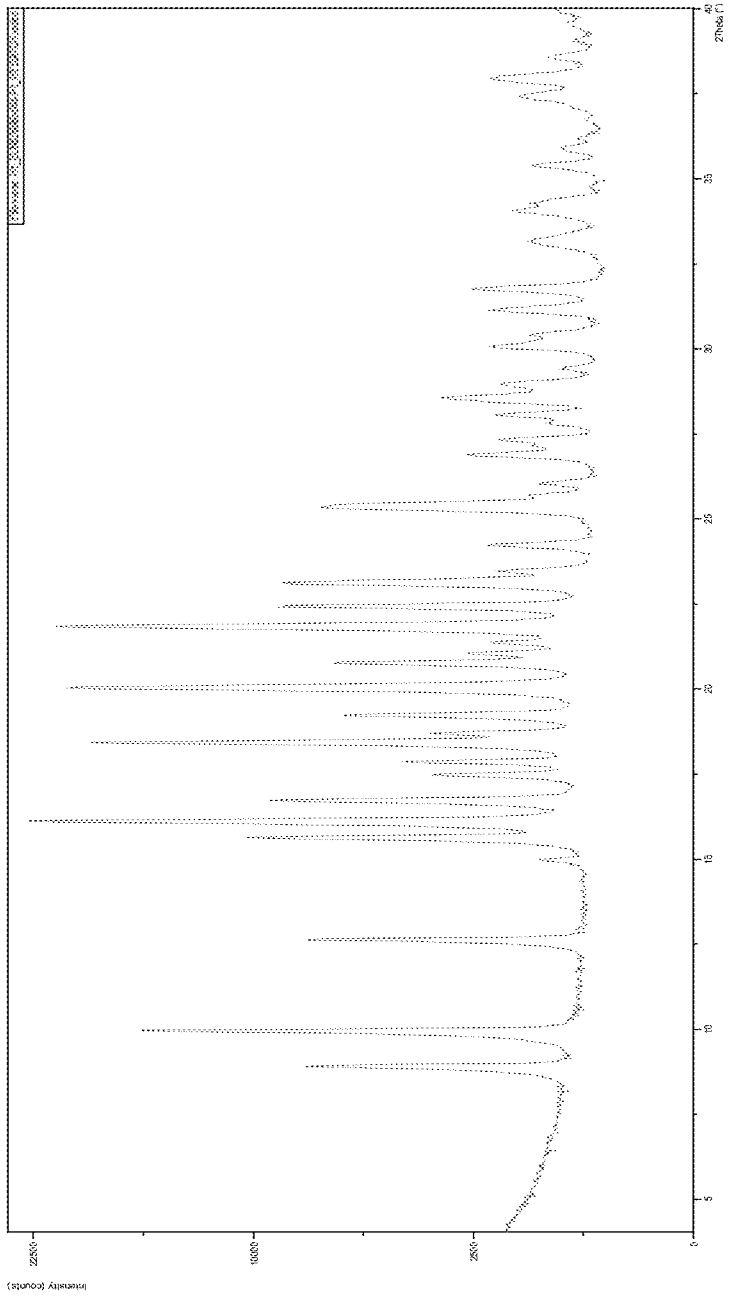
FIG. 1 X-ray powder diffraction pattern for Form A.

API Active Pharmaceutical Ingredient $(Boc)_2O$ Di-tert-butyl dicarbonate

DCM Dichloromethane

DEAD Diethyl azodicarboxylate

DIPEA N,N-Diisopropylethylamine

DMAc N,N-Dimethylacetamide

DMF Dimethylformamide

DSC Differential scanning calorimetry eq Equivalent

EtOAc or EA Ethyl acetate

EtOH Ethanol

FaSSIF Fasted State Simulated Intestinal Fluid

FeSSIF Fed State Simulated Intestinal Fluid

GC-MS Gas chromatography-mass spectrometry

IPA Isopropanol

IPAc Isopropyl acetate $K_2CO_3$ Potassium carbonate

KOAc Potassium acetate

KOH Potassium hydroxide

LiHMDS Lithium bis(trimethylsilyl)amide

MTBE Methyl tert-butyl ether

2-MeTHF 2-Methyltetrahydrofuran

MeOH Methanol

MOM Methoxymethyl acetal
$MgSO_4$ Magnesium sulfate
$Na_2CO_3$ Sodium carbonate
NaH Sodium hydrid
$NH_4Cl$ Ammonium Chloride
NaHMDS Sodium bis(trimethylsilyl)amide
NaOAc Sodium acetate
NaOH Sodium hydroxide
SFC Supercritical fluid chromatography
SGF Simulated Gastric Fluid
tBuOH tert-Butyl alcohol
TAA tert-Amyl alcohol
TEA Triethylamine
Tol Toluene
THF Tetrahydrofuran
TGA Thermal gravimetric analysis
UPLC Ultra Performance Liquid Chromatography
v/v Volume ratio
wt. % Weight percentage
XRPD X-ray powder diffraction The present invention provides an innovative process for preparing the compounds of formula (I) as outlined in the scheme 1.

The synthesis comprises the following steps:

step a) the formation of compound (III), (III)

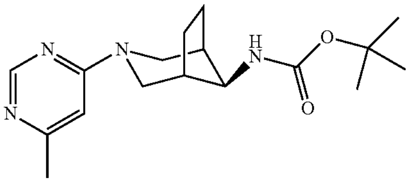

via the reaction of compound (II), (II)

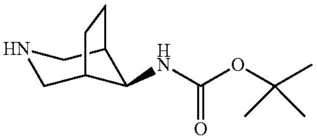

Scheme 1

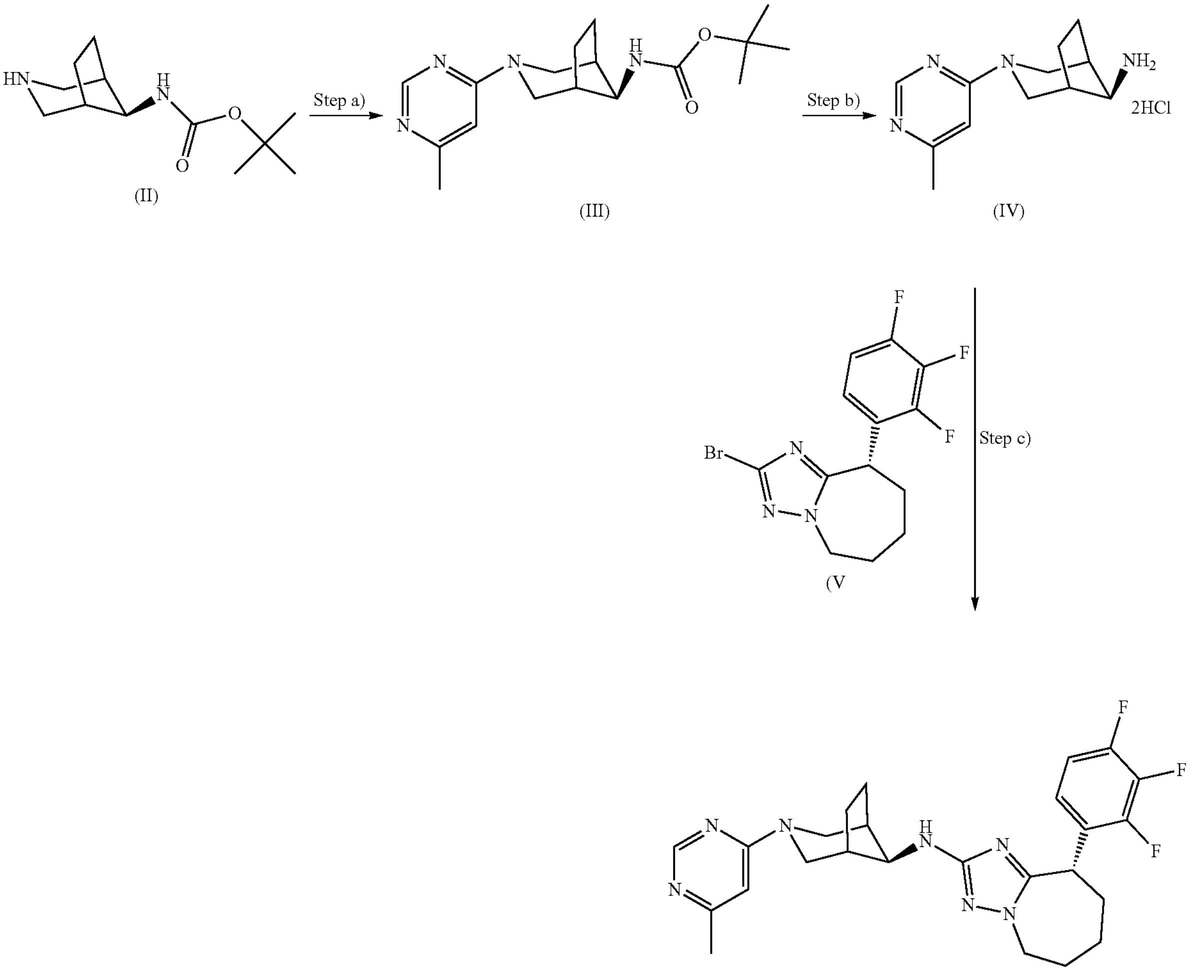

(II) (III) (IV) (V (I and 4-chloro-6-methyl-pyrimidine;

step b) the formation of compound (IV), (IV)

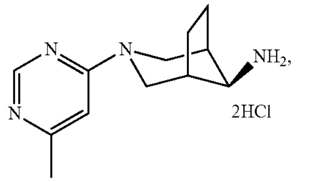

via de-protection reaction of compound (III) and formation of HCl salt;

step c) the cross coupling forming of compound (I), (I)

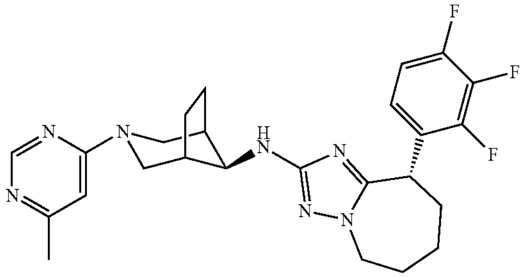

via Buchwald cross coupling reaction from compound (IV) and compound (V)

(V)

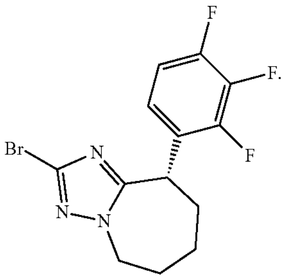

A detailed description of present invention of process steps is as following:

Step a) the formation of compound (III), (III)

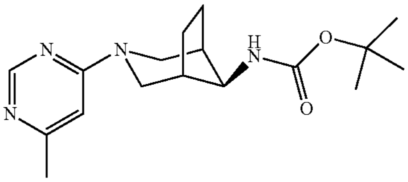

, via the reaction of compound (II), (II)

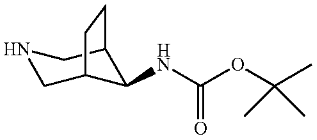

,

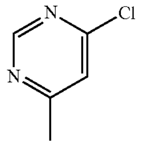

and 4-chloro-6-methyl-pyrimidine

Compound of formula (III) is synthesized in the presence of a suitable solvent with a suitable base.

The suitable solvent is selected from MeOH, IPA, tBuOH, and water (with 5% wt TPGS-750-M); preferably, the solvent is water (with 5% wt TPGS-750-M).

The suitable base is selected from KOAc, NaOAc, NaOH, KOH, $K_2CO_3$, $Na_2CO_3$, DIPEA and TEA, preferably the suitable base is TEA.

The reaction is performed at 0~120° C., preferably at 75~85° C., more preferably at 75~78° C. or 80~85° C.

A lot of impurity was detected while the NMP or EtOH was employed as solvent in the previous publications WO 2018060300 and WO 2019141832, which are unsuitable for large-scale manufacture due to difficult purification. In present invention, the suitable solvent, in particular Water (5% wt. TPGS-750-M), was employed to get the compound (III), which can be controlled well to isolate the product with simple filtration for large-scale manufacture.

Step b) the formation of compound (IV), (IV)

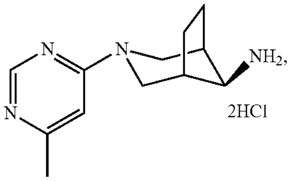

via deprotection reaction of compound (III) and formation of HCl salt.

Compound (IV) is synthesized in a suitable solvent with a suitable acid.

The suitable solvent is selected from DCM, THF, ACN and Acetone; preferably, the solvent is Acetone.

The suitable volume of solvent is from 5 to 15 V; preferably, the volume is 5V, 10 V, or 15V; more preferably, the volume is 10V.

The suitable acid is HCl; preferably, the acid is HCl (36.5% wt.).

The suitable equivalent of acid is from 5 to 15 eq; preferably, the equivalent is 5 eq, 6 eq, 10 eq, or 15 eq; more preferably, the equivalent is 6 eq.

The reaction is performed at −20~70° C., preferably at 0~25° C., more preferably at 20° C.

Solvent is critical for the whole process in terms of deprotection and isolation. In the patent publication WO 2019141832, TFA was employed as reagent; the product is difficult to be extracted from aqueous layer after neutralization, which directly results in the lower yield. While when the suitable solvent and the suitable acid of the present invention are used in the deprotection reaction, the product can be isolated with simple filtration, the purity and yield are improved significantly compared with the original one.

Step c) the formation of compound (I), (I)

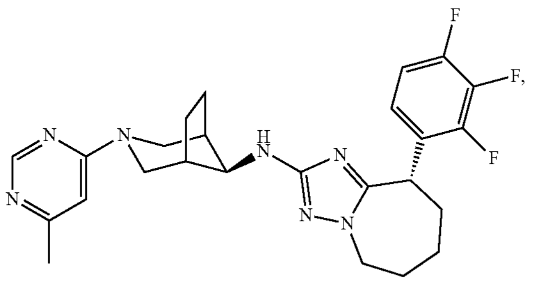

via Buchwald cross coupling reaction of compound (IV) and (V)

(V)

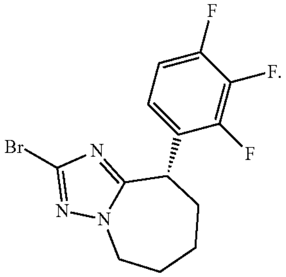

Compound (I) in this step is synthesized via Buchwald cross coupling reaction in the presence of a suitable base, catalyst, additive, and ligand in a suitable solvent. The compound (I) is purified through recrystallization which is performed in a suitable solvent. The palladium removing is performed in a suitable solvent with suitable metal scavenges.

The suitable base used in this cross coupling reaction is selected from $Na_2CO_3$, $K_2CO_3$, $NaHCO_3$, $KHCO_3$, NaOH, and KOH; preferably, the base is $K_2CO_3$; more preferably, the base is $K_2CO_3$ (200-300 mesh).

The additive is selected from $H_2O$, TEA, t-BuOH, IPA, PEG-400, TPGS-750-M, DMF, Glycerol and DMAc; preferably the additive is DMAc.

The suitable solvent is selected from IPAc, EtOAc, MTBE, Tol, THF, 2-MeTHF and TAA; preferably, the solvent is TAA.

The catalyst is selected from $Pd(OAc)_2$ and $Pd_2(dba)_3$; preferably, the catalyst is $Pd_2(dba)_3$.

The ligand is selected from BrettPhos, AdCyBrettPhos, tBuBrettPhos, AdBrettPhos, RocPhos, tBuXphos, BippyPhos, $Me_4$tBuXphos and $Me_3$MeOtBuXphos; preferably, the ligand is $Me_3$MeOtBuXphos.

The cross coupling reaction is performed at 20~102° C. for 1~16 hours, preferably at 100~102° C. for 2 hours.

The recrystallization is performed in a suitable solvent at 20~80° C. for 1~48 hours, preferably at 70~75° C. for 0.5 hours; wherein the suitable solvent is selected from heptane, hexane and petroleum ether; preferably, the solvent is heptane; more preferably, the solvent is n-heptane.

The metal scavengers used to remove residual Pd in the final product after the cross coupling reaction is selected from one or more of SiliaMetS Thiol, SiliaMetS DMT, SiliaBond Amine, SiliaMetS AMPA, SiliaMetS Cysteine, SiliaMetS DEAM, SiliaMetS Diamine, SiliaMetS DOTA, SiliaMetS Imidazole, SiliaMetS TAAcOH, SiliaMetS TAACONa, SiliaMetS Thiourea, SiliaBond Tosic Acid, SiliaMetS Triamine and MP-TMT; preferably the metal scavengers are SiliaMetS Thiol and SiliaMetS DMT.

The ligand and the reaction solvent of the present invention (in particular, $Me_3$MeOtBuXphos and TAA) help to improve the conversion and decrease the racemization risk in step c. The designed reaction condition in this invention can produce high yield and good chiral purity product (I).

EXAMPLES

The invention will be better understood by reference to the following examples. They should not, however, be construed as limiting the scope of the invention.

Example 1 tert-butyl N-[3-(6-methylpyrimidin-4-yl)-3-azabicyclo[3.2.1]octan-8-yl]carbamate (compound (III))

(III)

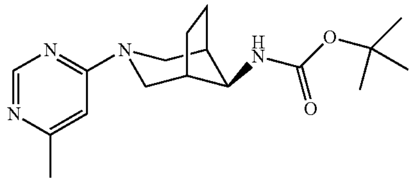

To a 5 L 4-neck vessel was charged with 4-chloro-6-metylpyrimidine (182 g, 1.39 mol) in water (2000 mL). And then to the resulting mixture was charged with tert-butyl (1R,5S,8s)-3-azabicyclo[3.2.1]octan-8-ylcarbamate (compound (II)) (334 g, 1.46 mol, Eq: 1.05), DL-alpha-tocopherol methoxypolyethylene glycol succinate (TPGS-750-M) (50 g) and triethylamine (573 g, 789 mL, 5.5 mol, Eq: 4). The resulting mixture was heated to reflux (80~85° C.) for 3 hrs., cooled to 20~25° C. and stirred for 14 hours. The product was collected via filter and washed with water (1000 ml), and dried in vacuum oven (30 mmHg, 50° C.) for 16 hours to afford compound (III) (433 g, 97.3% yield, 99.26% purity) as white solid.

Compound (III): $^1$H NMR (300 MHz, CHLOROFORM-d) ppm 1.46 (s, 11H) 1.50-1.66 (m, 3H) 1.70-1.88 (m, 2H) 2.35 (s, 6H) 3.04 (d, J=12.51 Hz, 2H) 3.80 (br. s., 1H) 4.11 (br. s., 2H) 4.44 (br. s., 1H) 6.33 (s, 1H) 8.49 (s, 1H).

Example 2 tert-butyl N-[3-(6-methylpyrimidin-4-yl)-3-azabicyclo[3.2.1]octan-8-yl]carbamate (compound (III))

(III)

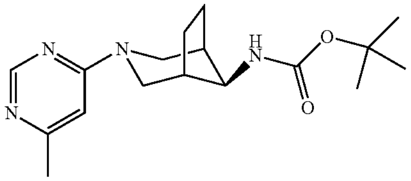

To a 50 L reactor was charged with 4-chloro-6-metylpyrimidine (1.8 kg, 14.0 mol) in water (18 L), and then to the resulting mixture was charged with tert-butyl (1R,5S,8s)-3-azabicyclo[3.2.1]octan-8-ylcarbamate (compound (II)) (3.3 kg, 14.7 mol), DL-alpha-tocopherol methoxypolyethylene glycol succinate (TPGS-750-M) (0.36 kg) and triethylamine (5.67 kg). The resulting mixture was heated to 75~78° C. for 3 hours, cooled to 20~25° C. and stirred for 16 hours. The product was collected via filter and washed with water (3.6 kg, and dried in vacuum oven (30 mmHg, 50° C.) for 16 hours to afford compound (III) (4.25 kg, % yield, >99.0% purity).

Compound (III): $^{1}$H NMR (300 MHz, CHLOROFORM-d) ppm 1.46 (s, 11H) 1.50-1.66 (m, 3H) 1.70-1.88 (m, 2H) 2.35 (s, 6H) 3.04 (d, J=12.51 Hz, 2H) 3.80 (br. s., 1H) 4.11 (br. s., 2H) 4.44 (br. s., 1H) 6.33 (s, 1H) 8.49 (s, 1H).

Example 3

3-(6-methylpyrimidin-4-yl)-3-azabicyclo[3.2.1]octan-8-amine; dihydrochloride (compound (IV))

(IV)

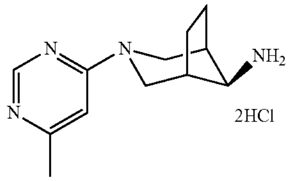

To a 2 L 3-neck vessel was charged with tert-butyl ((1R,5S,8S)-3-(6-methylpyrimidin-4-yl)-3-azabicyclo[3.2.1]octan-8-yl)carbamate (40 g, 126 mmol) in acetone (0.8 L). To the resulting mixture was added HCl (36.5% wt., 62.7 mL, 754 mmol, Eq: 6). The resulting reaction mixture was stirred at 20~25° C. for 16 hours. Large amount of white solid was precipitated out. The product was collected via filtration. The filter cake was washed with acetone (100 ml) and dried in vacuum oven (30 mmHg, 50° C.) for 16 hours to afford compound (IV) (27 g, 73.1% yield, 99% purity) as pale solid.

Compound (IV): $^{1}$H NMR (400 MHz, DMSO-$d_6$) δ=8.77 (s, 1H), 8.61-8.42 (m, 3H), 7.17 (s, 1H), 4.71 (br s, 1H), 4.04 (br s, 1H), 3.58 (br d, J=5.3 Hz, 2H), 3.53-3.33 (m, 3H), 3.22 (br s, 1H), 2.58-2.53 (m, 2H), 2.45 (s, 3H), 2.04-1.92 (m, 2H), 1.40 (br s, 2H).

Example 4

3-(6-methylpyrimidin-4-yl)-3-azabicyclo[3.2.1]octan-8-amine; dihydrochloride (compound (IV))

(IV)

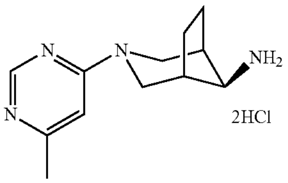

To a 10 L 4-neck vessel was charged with tert-butyl ((1R,5S,8S)-3-(6-methylpyrimidin-4-yl)-3-azabicyclo[3.2.1]octan-8-yl)carbamate (432 g, 1.34 mmol) in acetone (8.6 L), the resulting reaction mixture was stirred at 20~25° C. for 0.5 hours. And then, to the resulting mixture was added HCl (36.5% wt., 671 mL, 8.06 mol, Eq: 6) and was stirred at 20~25° C. for 16 hours. Large amount of white solid was precipitated out. The product was collected via filtration. The filter cake was washed with acetone (500 ml) and dried in vacuum oven (30 mmHg, 50° C.) for 16 hours to afford compound (IV) (417 g, 99.7% yield, 99.27% purity) as pale solid.

Compound (IV): $^{1}$H NMR (400 MHz, DMSO-$d_6$) δ=8.77 (s, 1H), 8.61-8.42 (m, 3H), 7.17 (s, 1H), 4.71 (br s, 1H), 4.04 (br s, 1H), 3.58 (br d, J=5.3 Hz, 2H), 3.53-3.33 (m, 3H), 3.22 (br s, 1H), 2.58-2.53 (m, 2H), 2.45 (s, 3H), 2.04-1.92 (m, 2H), 1.40 (br s, 2H).

Example 5

3-(6-methylpyrimidin-4-yl)-3-azabicyclo[3.2.1]octan-8-amine; hydrate; dihydrochloride (compound (IV))

(IV)

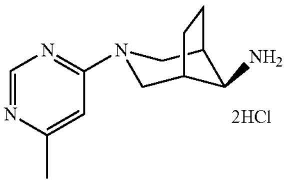

To a 50 L reactor was charged with tert-butyl ((1R,5S,8S)-3-(6-methylpyrimidin-4-yl)-3-azabicyclo[3.2.1]octan-8-yl)carbamate (1.4 kg, 4.35 mol) in acetone (22.1 kg), the resulting reaction mixture was stirred at 20~25° C. for 0.5 hours. And then, to the resulting mixture was added HCl (36.5% wt., 2.61 kg, 26.1 mol, Eq: 6) and was stirred at 20~30° C. 16 hours. Large amount of white solid precipitated out. The product was collected via filtration. The filter cake was washed with acetone (3×1.4 L) and dried in vacuum oven (30 mmHg, 50° C.) for 16 hours to afford compound (IV) (1.33 kg, 4.3 mol, 98% yield, 99.84% purity) as pale solid.

Compound (IV): $^{1}$H NMR (400 MHz, DMSO-$d_6$) δ=8.77 (s, 1H), 8.61-8.42 (m, 3H), 7.17 (s, 1H), 4.71 (br s, 1H), 4.04

(br s, 1H), 3.58 (br d, J=5.3 Hz, 2H), 3.53-3.33 (m, 3H), 3.22 (br s, 1H), 2.58-2.53 (m, 2H), 2.45 (s, 3H), 2.04-1.92 (m, 2H), 1.40 (br s, 2H).

Example 6

(9S)-N-[3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (compound (I))

(I)

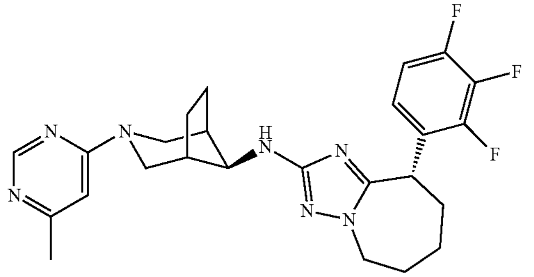

To a 250 mL vessel was charged with compound (IV) (9.83 g, 31.8 mmol, Eq: 1.1) in water (20 mL), and then saturated $K_2CO_3$ (30 mL) was added slowly at 20~25° C. The resulting reaction mixture was stirred at 20~25° C. for 0.5 hours, pH about 8~10. The resulting mixture was separated and the aqueous layer was extracted with n-BuOH (30 mL) three times. The combined organic layers were washed with brine (30 mL, 16.5% wt.). The aqueous was separated and the organic layer was concentrated to remove solvent. The residual was diluted with tert-amyl alcohol (50 mL), and then concentrated again. The resulting diluted with tert-amyl alcohol (50 mL), the resulting mixture will charge to a 5 L 3-neck reactor.

To a 5 L reactor was equipped with mechanical stirrer were charged with $Pd_2(dba)_3$ (2.6 g, 2.9 mmol, Eq: 0.1), $MeOMe_3$tButylXphos (2.8 g, 5.8 mmol, Eq: 0.2), potassium carbonate (9.6 g, 69.3 mmol, Eq: 2.4) and tert-Amyl alcohol (80 g). The resulting mixture was purged with $N_2$ three times. The reaction mixture was heated to 100~102° C. and stirred at that temperature for 0.5 hours. To the reaction mixture was added the (R)-2-bromo-9-(2,3,4-trifluorophenyl)-6,7,8,9-tetrahydro-5H-[1,2,4]triazolo[1,5-a]azepine (10 g, 28.9 mmol, Eq: 1) and N,N-Dimethylacetamide (6 ml). The resulting reaction mixture was heated to reflux for another 2 h. LC-MS indicated the sm/product <5%; Chiral purity was 99.41%. 2-MeTHF (100 mL) was added. The reaction mixture was cooled to 20~25° C. Water (100 mL) was added, separated. The resulting organic layer was washed with N-acytyl cysteine solution (N-acetyl cysteine (1.5 g)+$K_2CO_3$ (1.5 g)+water (100 mL)) 3 times. The resulting mixture was filter through celite pad; then concentrated to remove solvent. The residual was diluted with IPAc (40 mL), and then heated to 70~75° C. To the reaction was added heptane (240 mL, 24 V) at 70~75° C. Large amount of solid precipitate out; stirred at 70~75° C. for another 0.5 h, and let the reaction mixture slowly cooled down to 20~25° C. and stirred for another 16 hours at that temperature. The resulting cake was collected by filtration and the cake was rinsed with heptane (2-3 v).

To a 500 mL reactor were charged with crude compound (I) (10 g) in EtOH (200 mL). The result reaction mixture was heated to 70~75° C., clear brown solution was obtained. To the reaction mixture was added active carbon (30% wt, 3 g) and silaMetDMT (30% wt, 3 g), and then result reaction mixture was stirred at 70~75° C. for another 4 hours. Cooled to 50° C. Filtered through celite pad. The cake was rinsed with hot EtOH (50~55° C.; 20 mL). To a 3 L reactor was charge the resulting solution and sialeMet thiol (40% wt, 4 g)). The resulting reaction mixture was heated to 70~75° C. for another 4 hours. Cooled to 50~55° C. Filtered through celite pad. The cake was rinsed with hot EtOH (50~55° C.; 20 mL). The resulting mixture was concentrated.

To a 500 mL reactor were charged with the residual in ethanol (30 mL). The result reaction mixture was heated to 70~75° C., clear brown solution was obtained. And then the reaction mixture was slowly cooled down to 20~25° C. To the reaction mixture was added water (100 mL). The result reaction mixture was stirred at 20~25° C. for 16 hours. The product was collected via filter and washed with water (30 g), and dried in vacuum oven (30 mmHg, 50° C.) for 16 hours to afford compound (I) (8.6 g, 99.80% by HPLC purity, ee %: 98.74%, 60.9% yield).

Compound (I): $^1$H NMR (400 MHz, DMSO-$d_6$) δ ppm 1.25 (br d, J=7.70 Hz, 2H) 1.46-1.65 (m, 1H) 1.68-1.88 (m, 2H) 1.74-1.85 (m, 1H) 1.88-2.12 (m, 3H) 1.98-2.08 (m, 1H) 2.24 (s, 3H) 2.36 (br s, 2H) 2.90 (br d, J=12.23 Hz, 2H) 3.45 (d, J=3.91 Hz, 1H) 3.88-4.17 (m, 3H) 4.24 (br dd, J=14.24, 3.73 Hz, 1H) 4.31-4.39 (m, 1H) 5.76 (d, J=4.16 Hz, 1H) 6.60 (s, 1H) 7.16-7.25 (m, 1H) 7.25-7.33 (m, 1H) 8.33 (s, 1H)

$^{13}$C NMR (101 MHz, DMSO-$d_6$) δ ppm 24.19 (s, 1 C) 25.69 (s, 1 C) 25.74 (s, 1 C) 27.36 (s, 1 C) 29.10 (s, 1 C) 31.67 (s, 1 C) 38.28 (s, 1 C) 38.66 (s, 1 C) 38.74 (s, 1 C) 50.03 (s, 1 C) 50.61 (s, 2 C) 62.24 (s, 1 C) 101.90 (s, 1 C) 112.57 (dd, J=16.10, 2.90 Hz, 1 C) 124.40-124.88 (m, 1 C) 127.74 (dd, J=11.70, 3.70 Hz, 1 C) 139.36 (dt, J=247.41, 15.68 Hz, 1 C) 149.26 (br dd, J=247.00, 11.00 Hz, 1 C) 149.53 (dd, J=247.00, 11.00 Hz, 1 C) 155.58 (s, 1 C) 157.61 (s, 1C) 161.55 (s, 1 C) 163.19 (s, 1 C) 164.72 (s, 1 C)

$^{19}$F NMR (376 MHz, DMSO-$d_6$) δ ppm −162.58 (td, J=21.67, 6.94 Hz, 1 F) −138.02 (ddd, J=15.61, 10.41, 5.20 Hz, 1 F) −136.27 (br d, J=20.80 Hz, 1 F)

$[\alpha]D^{25}$=16.973°

HRMS: calculated 483.236 $[C_{25}H_{28}F_3N_7+H]^+$, found 484.2448 $[M+H]^+$

Example 7

(9S)-N-[3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (compound (I))

(I)

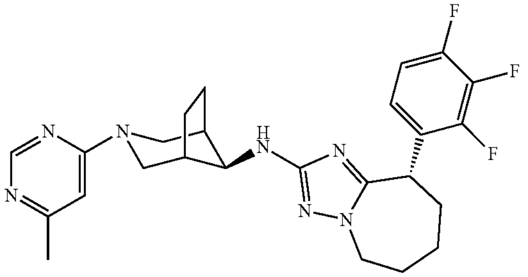

To a 3 L vessel was charged with compound (IV) (98.3 g, 318 mmol, Eq: 1.1) in water (200 mL), and then saturated $K_2CO_3$ (300 mL) was added slowly at 20~25° C. The resulting reaction mixture was stirred at 20~25° C. for 0.5 hours, pH about 8~10. The resulting mixture was separated and the aqueous layer was extracted with n-BuOH (300 mL) three times. The combined organic layers were washed with brine (300 mL, 16.5% wt.). The aqueous was separated and the organic layer was concentrated to remove solvent. The residual was diluted with tert-amyl alcohol (500 mL), and then concentrated again. The resulting diluted with tert-amyl alcohol (500 mL), the resulting mixture will charge to a 5 L, 3-neck reactor.

To the above 5 L reactor equipped with mechanical stirrer were charged with $Pd_2(dba)_3$ (26.5 g, 28.9 mmol, Eq: 0.1), $MeOMe_3$tButylXphos (28.7 g, 57.8 mmol, Eq: 0.2), potassium carbonate (95.8 g, 693 mmol, Eq: 2.4). The resulting mixture was purged with $N_2$ three times. The reaction mixture was heated to 100~102° C. and stirred at that temperature for 0.5 hours. To the reaction mixture was added the (R)-2-bromo-9-(2,3,4-trifluorophenyl)-6,7,8,9-tetrahydro-5H-[1,2,4]triazolo[1,5-a]azepine (100 g, 289 mmol, Eq: 1) and N,N-Dimethylacetamide (70 ml). The resulting reaction mixture was heated to reflux for another 2 h. LC-MS indicated the sm/product <5%; Chiral purity was 99.41%. 2-MeTHF (1 L) was added. The reaction mixture was cooled to 20~25° C. Water (1 L) was added, separation. The resulting organic layer was washed with N-acytyl cysteine solution (N-acetyl cysteine (15 g)+$K_2CO_3$ (15 g)+water (1 L)) 3 times. The resulting mixture was filtered through celite pad; then concentrated to remove solvent. The residual was diluted with IPAc (400 mL), and then heated to 70~75° C. To the reaction was added heptane (2400 mL, 24 V) 70~75° C. Large amount of solid precipitate out; stirred at 70~75° C. for another 0.5 h, and let the reaction mixture slowly cooled down to 20~25° C. and stirred for another 16 hours at that temperature. The resulting cake was collected by filtration and the cake was rinsed with heptane (2-3 v).

To a 3 L reactor was charged with crude compound (I) (101 g) in EtOH (2 L). The result reaction mixture was heated to 70~75° C., clear brown solution was obtained. To the reaction mixture was added active carbon (30% wt, 30 g) and silaMetDMT (30% wt, 30 g), and then result reaction mixture was stirred at 70~75° C. for another 4 hours. Cooled to 50° C. Filtered through celite pad. The cake was rinsed with hot EtOH (50~55° C.; 200 mL). To a 3 L reactor was charge the resulting solution and sialeMet thiol (40% wt, 40 g)). The resulting reaction mixture was heated to 70~75° C. for another 4 hours. Cooled to 50~55° C. Filtered through celite pad. The cake was rinsed with hot EtOH (50~55° C.; 200 mL). The resulting mixture was concentrated.

To a 3 L reactor was charged with the residual in ethanol (300 mL). The result reaction mixture was heated to 70~75° C., clear brown solution was obtained. And then the reaction mixture was slowly cooled down to 20~25° C. To the reaction mixture was added water (1 L). The result reaction mixture was stirred at 20~25° C. for 16 hours The product was collected via filter and washed with water (0.3 kg), and dried in vacuum oven (30 mmHg, 50° C.) for 16 hours to afford compound (I) (90 g, 99.80% by HPLC purity, ee %: 98.74%, assay: 99.41%, KF: 0.10%, heavy metal (Pd): 18 ppm, crystal form: form A, 64.3% yield).

Compound (I): $^1$H NMR (400 MHz, DMSO-$d_6$) δ ppm 1.25 (br d, J=7.70 Hz, 2H) 1.46-1.65 (m, 1H) 1.68-1.88 (m, 2H) 1.74-1.85 (m, 1H) 1.88-2.12 (m, 3H) 1.98-2.08 (m, 1H) 2.24 (s, 3H) 2.36 (br s, 2H) 2.90 (br d, J=12.23 Hz, 2H) 3.45 (d, J=3.91 Hz, 1H) 3.88-4.17 (m, 3H) 4.24 (br dd, J=14.24, 3.73 Hz, 1H) 4.31-4.39 (m, 1H) 5.76 (d, J=4.16 Hz, 1H) 6.60 (s, 1H) 7.16-7.25 (m, 1H) 7.25-7.33 (m, 1H) 8.33 (s, 1H)

$^{13}$C NMR (101 MHz, DMSO-$d_6$) δ ppm 24.19 (s, 1 C) 25.69 (s, 1 C) 25.74 (s, 1 C) 27.36 (s, 1 C) 29.10 (s, 1 C) 31.67 (s, 1 C) 38.28 (s, 1 C) 38.66 (s, 1 C) 38.74 (s, 1 C) 50.03 (s, 1 C) 50.61 (s, 2 C) 62.24 (s, 1 C) 101.90 (s, 1 C) 112.57 (dd, J=16.10, 2.90 Hz, 1 C) 124.40-124.88 (m, 1 C) 127.74 (dd, J=11.70, 3.70 Hz, 1 C) 139.36 (dt, J=247.41, 15.68 Hz, 1 C) 149.26 (br dd, J=247.00, 11.00 Hz, 1 C) 149.53 (dd, J=247.00, 11.00 Hz, 1 C) 155.58 (s, 1 C) 157.61 (s, 1C) 161.55 (s, 1 C) 163.19 (s, 1 C) 164.72 (s, 1 C)

$^{19}$F NMR (376 MHz, DMSO-$d_6$) δ ppm −162.58 (td, J=21.67, 6.94 Hz, 1 F) −138.02 (ddd, J=15.61, 10.41, 5.20 Hz, 1 F) −136.27 (br d, J=20.80 Hz, 1 F)

[α]D$^{25}$=16.973°

HRMS: calculated 483.236 [$C_{25}H_{28}F_3N_7$+H]$^+$, found 484.2448 [M+H]$^+$

Example 8

(9S)-N-[3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (compound (I))

(I)

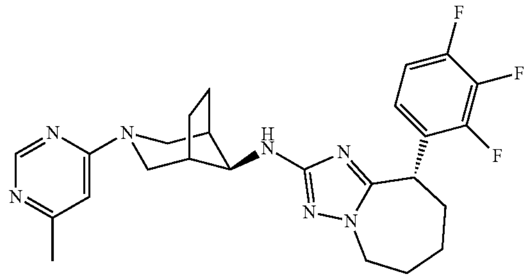

To a 20 L vessel was charged with compound (IV) (540 g, 1.75 mmol, Eq: 1.1), n-BuOH (2.24 kg) in Water (1.1 L), and then saturated $K_2CO_3$ (1.1 L) was added slowly at 20~30° C. The resulting reaction mixture was stirred at 20~30° C. for 0.5 hours to get a pH about 8~10 solution. The solution was separated and the aqueous layer was extracted with n-BuOH (1.34 kg). The combined organic layers were washed with brine (2.75 kg, 16.5% wt.). The organic layer was concentrated, residual was diluted with tert-amyl alcohol (2.24 kg), and then concentrated again for three times. The residual was diluted with tert-amyl alcohol (5.5 L) in the 12 L reactor.

To the above 12 L reactor was equipped with mechanical stirrer were charged with $Pd_2(dba)_3$ (145 g, 159 mmol, Eq: 0.1), $MeOMe_3$tButylXphos (155 g, 318 mmol, Eq: 0.2), potassium carbonate (540 g, 3.97 mol, Eq: 2.5). The resulting mixture was purged with $N_2$ three times. The reaction mixture was heated to 100~102° C. and stirred at that temperature for 0.5 hours. To the reaction mixture was added the (R)-2-bromo-9-(2,3,4-trifluorophenyl)-6,7,8,9-tetrahydro-5H-[1,2,4]triazolo[1,5-a]azepine (550 g, 1.59 mol, Eq: 1) and N,N-Dimethylacetamide (385 ml). The resulting reaction mixture was heated to reflux for another 2 h. LC-MS indicated the sm/product <5%; Chiral purity was 99.41%. 2-MeTHF (4.7 kg) was added. The reaction mixture was cooled to 20~25° C. 2-MeTHF (4.7 kg) and water (5.5 kg) were added. The organic layer was separated and washed with N-acytyl cysteine solution (N-acetyl cysteine 82.5 g+$K_2CO_3$ 82.5 g+water 5.5 kg) three times and brine (5.5 kg) twice. The resulting mixture was filter through celite pad; then concentrated to remove solvent. The residual was diluted with IPAc (1.91 kg), and then heated to 70~75° C. To the reaction was added heptane (9.02 kg) at 70~75° C. Large amount of solid precipitate out; stirred at 70~75° C. for another 0.5 h, and let the reaction mixture slowly cooled down to 20~25° C. and stirred for another 16 hours at that temperature. The resulting cake was collected by filtration and the cake was rinsed with heptane (1.12 kg).

To a 50 L reactor was charged with crude compound (I) in EtOH (8.68 kg). The result reaction mixture was heated to 70~78° C., clear brown solution was obtained. To the reaction mixture was added active carbon (165 g) and silaMetDMT (165 g), and then resulting reaction mixture was stirred at 70~75° C. for another 4 hours. Cooled to 50~55° C. Filtered through celite pad. The cake was rinsed with hot EtOH (50~55° C.; 0.87 kg). To a 50 L reactor was charge the resulting solution and sialeMet thiol (40% wt, 165 g). The resulting reaction mixture was heated to 70~75° C. for another 4 hours. Cooled to 50~55° C. Filtered through celite pad. The cake was rinsed with hot EtOH (50~55° C.; 0.87 kg). The resulting mixture was concentrated.

To a 20 L reactor was charged with the residual in ethanol (1.22 kg). The result reaction mixture was heated to 70~75° C., then the reaction mixture was slowly cooled down to 20° C. To the reaction mixture was added water (5.5 kg). The result reaction mixture was stirred at 20~25° C. for 16 hours. The product was collected via filter and washed with water (1.1 kg), and dried in vacuum oven (30 mmHg, 50° C.) for 16 hours to afford compound (I) (425 g, 99.80% by HPLC purity, ee %: 98.74%, assay: 99.41%, KF: 0.10%, heavy metal (Pd): 30 ppm, crystal form: form A, 55.30% yield).

Compound (I): $^1$H NMR (400 MHz, DMSO-$d_6$) δ ppm 1.25 (br d, J=7.70 Hz, 2H) 1.46-1.65 (m, 1H) 1.68-1.88 (m, 2H) 1.74-1.85 (m, 1H) 1.88-2.12 (m, 3H) 1.98-2.08 (m, 1H) 2.24 (s, 3H) 2.36 (br s, 2H) 2.90 (br d, J=12.23 Hz, 2H) 3.45 (d, J=3.91 Hz, 1H) 3.88-4.17 (m, 3H) 4.24 (br dd, J=14.24, 3.73 Hz, 1H) 4.31-4.39 (m, 1H) 5.76 (d, J=4.16 Hz, 1H) 6.60 (s, 1H) 7.16-7.25 (m, 1H) 7.25-7.33 (m, 1H) 8.33 (s, 1H)

$^{13}$C NMR (101 MHz, DMSO-$d_6$) δ ppm 24.19 (s, 1 C) 25.69 (s, 1 C) 25.74 (s, 1 C) 27.36 (s, 1 C) 29.10 (s, 1 C) 31.67 (s, 1 C) 38.28 (s, 1 C) 38.66 (s, 1 C) 38.74 (s, 1 C) 50.03 (s, 1 C) 50.61 (s, 2 C) 62.24 (s, 1 C) 101.90 (s, 1 C) 112.57 (dd, J=16.10, 2.90 Hz, 1 C) 124.40-124.88 (m, 1 C) 127.74 (dd, J=11.70, 3.70 Hz, 1 C) 139.36 (dt, J=247.41, 15.68 Hz, 1 C) 149.26 (br dd, J=247.00, 11.00 Hz, 1 C) 149.53 (dd, J=247.00, 11.00 Hz, 1 C) 155.58 (s, 1 C) 157.61 (s, 1C) 161.55 (s, 1 C) 163.19 (s, 1 C) 164.72 (s, 1 C)

$^{19}$F NMR (376 MHz, DMSO-$d_6$) δ ppm −162.58 (td, J=21.67, 6.94 Hz, 1 F) −138.02 (ddd, J=15.61, 10.41, 5.20 Hz, 1 F) −136.27 (br d, J=20.80 Hz, 1 F)

[α]$D^{25}$=16.973°

HRMS: calculated 483.236 $[C_{25}H_{28}F_3N_7+H]^+$, found 484.2448 $[M+H]^+$

Example 9

Characterization of Form a of Compound (I)

Characterization method:

DSC analysis:

TA instrument DSC Q2000

Scanning range: 30-350° C.

Ramp: 10° C./min

TGA analysis:

TA instrument TGA Q5000

Scanning range: 30-350° C.,

Ramp: 10° C./min.

XRPD:

PANalytical Empyrean XRPD

X-ray source: Cu Kα (λ=1.5406 Å)

Working electricity: 40 mA

Working voltage: 40 kV

Detector: PSD

Scanning scope: 4 to 40 degree (2 Theta)

Scanning step: 0.05 degree/step (2 Theta)

Scanning speed: 1 step/sec

TABLE 1

X-Ray Powder Diffraction peaks of Form A of compound (I).

| Pos. [°2Th.] | Rel. Int. [%] |
|---|---|
| 8.9 | 20.3 |
| 9.7 | 4.6 |
| 10.0 | 47.5 |
| 12.6 | 25.2 |
| 15.0 | 3.0 |
| 15.6 | 30.3 |
| 16.1 | 100.0 |
| 16.5 | 7.9 |
| 16.7 | 29.7 |
| 17.5 | 9.1 |
| 17.9 | 11.3 |
| 18.4 | 40.0 |
| 18.7 | 11.8 |
| 19.1 | 8.3 |
| 19.3 | 40.3 |
| 20.1 | 59.2 |
| 20.8 | 20.2 |
| 21.1 | 8.1 |
| 21.3 | 4.6 |
| 21.8 | 39.7 |
| 22.5 | 18.2 |
| 23.2 | 19.2 |
| 23.5 | 3.7 |
| 24.2 | 6.3 |
| 25.3 | 16.3 |
| 25.4 | 14.5 |
| 25.7 | 3.9 |
| 26.0 | 1.8 |
| 26.1 | 2.4 |
| 26.9 | 6.8 |
| 27.3 | 2.8 |
| 27.8 | 1.8 |
| 28.0 | 3.7 |
| 28.4 | 7.1 |
| 28.6 | 8.6 |
| 29.0 | 3.8 |
| 29.4 | 1.2 |
| 30.0 | 7.7 |
| 30.4 | 2.0 |
| 31.1 | 7.6 |
| 31.7 | 5.9 |
| 31.8 | 5.6 |
| 33.1 | 2.8 |
| 34.0 | 1.9 |
| 34.3 | 3.8 |
| 35.4 | 2.3 |
| 37.3 | 2.3 |
| 37.4 | 3.0 |
| 37.8 | 4.8 |
| 38.0 | 7.9 |
| 38.6 | 1.8 |
| 39.1 | 2.0 |

Figure 2:
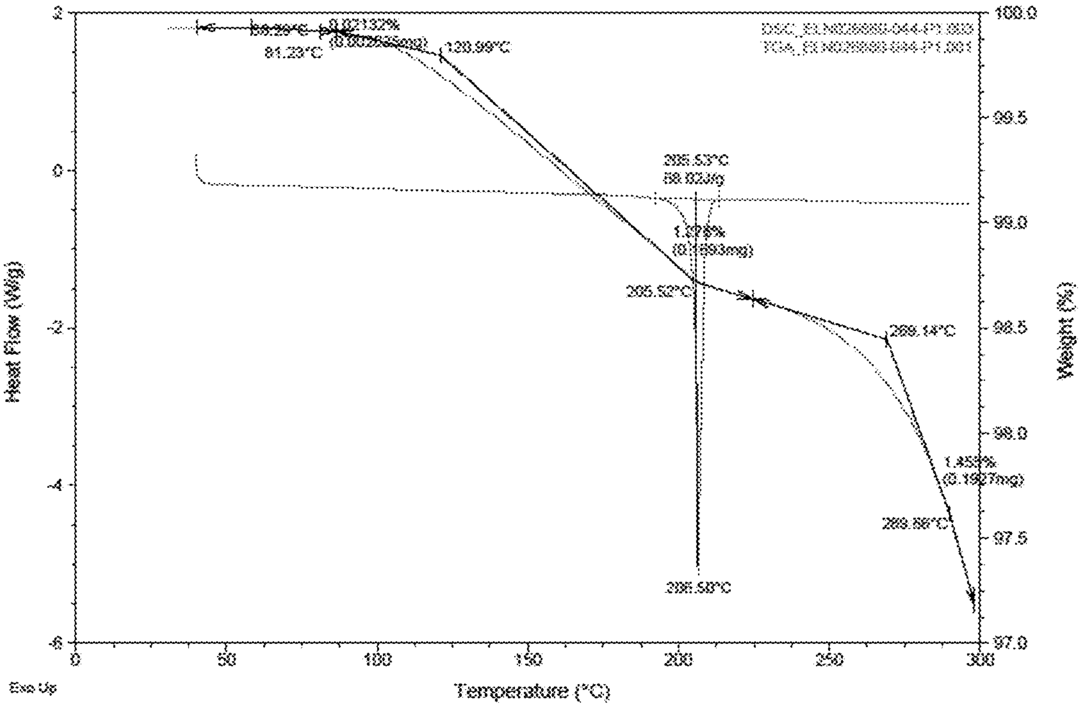
FIG. 2 DSC and TGA of Form A.

DSC result shown in FIG. 2 indicates Form A of compound (I) has an onset melting temperature at around 205.5° C.

Example 10

Solubility Study a. Testing Media pH 1.00 buffer pH 3.00 buffer pH 5.00 buffer pH 7.00 buffer pH 9.00 buffer Water SGF without Triton FaSSIF FeSSIF b. Testing Procedure Report No.: AD-GSM-046v01

Weigh about 5 mg of compound (I) into glass vial and add 0.5 ml testing medium listed above to form suspension. Shake these suspensions at 1200 rpm for about 24 hours under 25° C.

At the end of 24 hours, pull out all the vials and filter the suspensions by 0.22 μm PVDF filters. Check the pH value and concentration of filtrate by pH meter and UPLC respectively.

c. UPLC Condition

Chromatographic Parameters

| | | | |
|---|---|---|---|
| Instrument | Waters UPLC with DAD detector | | |
| Column | Waters BEH C18 (2.1 × 50 mm × 1.7 μm) | | |
| Oven temperature | 30° C. | | |
| Mobile phase | A: 0.1% FA in water | | |
| | B: 0.1% FA in ACN | | |
| | Time (min) | A % | B % |
| Gradient program | Initial | 95 | 5 |
| | 0.1 | 95 | 5 |
| | 2.0 | 5 | 95 |
| | 2.5 | 5 | 95 |
| | 2.51 | 95 | 5 |
| | 3.0 | 95 | 5 |
| Flow rate | 0.8 ml/min | | |
| Detector | UV 269 nm | | |
| Nominal concentration | 0.1 mg/ml | | |
| Injection volume | 2 μL | | |

d. Results

The solubility results are listed in Table 2. The result indicates the solubility is pH dependent.

TABLE 2

| Solubility results of Form A | | | |
|---|---|---|---|
| Test Medium | Solubility (mg/mL) | | Final pH |
| pH 1.0 buffer | >10 | >10 | 1.2 |
| | >10 | | 1.1 |
| | >10 | | 1.0 |
| pH 3.0 buffer | 5.366 | 5.347 ± 0.047 | 3.4 |
| | 5.468 | | 3.4 |
| | 5.477 | | 3.5 |
| pH 5.0 buffer | 0.091 | 0.101 ± 0.009 | 4.9 |
| | 0.097 | | 5.0 |
| | 0.114 | | 5.1 |
| pH 7.0 buffer | 0.007 | 0.006 ± 0.000 | 7.0 |
| | 0.006 | | 6.9 |
| | 0.006 | | 7.0 |
| pH 9.0 buffer | 0.006 | 0.006 ± 0.000 | 9.0 |
| | 0.006 | | 9.0 |
| | 0.006 | | 9.0 |
| Water | 0.007 | 0.006 ± 0.000 | 8.2 |
| | 0.006 | | 8.6 |
| | 0.006 | | 8.4 |
| SGF without Triton-X100 | >10 | >10 | 1.5 |
| | >10 | | 1.5 |
| | >10 | | 1.5 |
| FaSSIF | 0.034 | 0.033 ± 0.000 | 6.7 |
| | 0.034 | | 6.6 |
| | 0.033 | | 6.6 |
| FeSSIF | 0.614 | 0.618 ± 0.007 | 5.2 |
| | 0.611 | | 5.2 |
| | 0.628 | | 5.2 |

TABLE 2-continued

The invention claimed is:

1. A process for the preparation of a compound (I), (I)

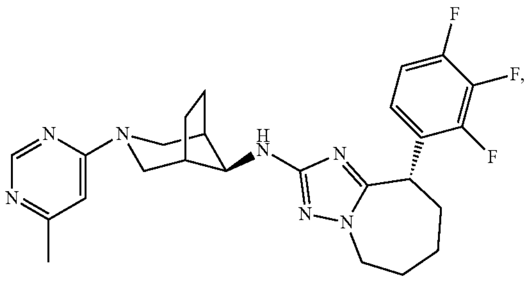

comprising the following steps:

step a) formation of compound (III), (III)

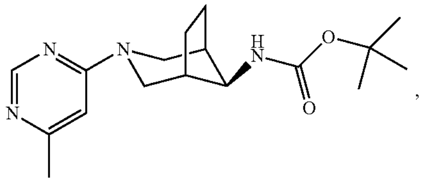

, via the reaction of compound (II), (II)

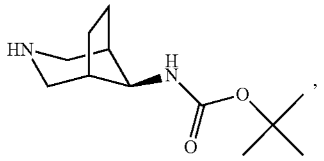

, and 4-chloro-6-methyl-pyrimidine;

step b) formation of compound (IV), (IV)

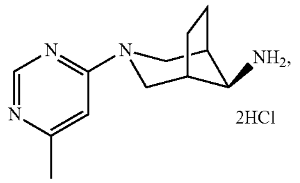

via de-protection reaction of compound (III) and formation of HCl salt;

step c) cross coupling forming of compound (I), (I)

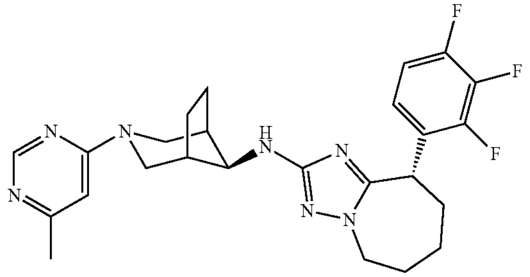

via Buchwald cross coupling reaction from compound (IV) and compound (V)

(V)

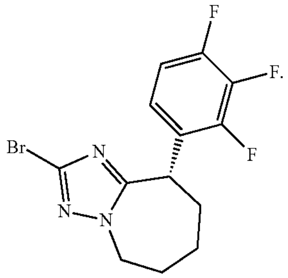

2. The process according to claim 1, characterized in that the formation of compound (III) in step a) is performed in the presence of a solvent, wherein the solvent is selected from the group consisting of MeOH, IPA, tBuOH, and water with 5% wt TPGS-750-M.

3. The process according to claim 1, characterized in that the formation of compound (III) in step a) is performed in the presence of a base, wherein base is selected from the group consisting of KOAc, NaOAc, NaOH, KOH, $K_2CO_3$, $Na_2CO_3$, DIPEA and TEA.

4. The process according to claim 1, characterized in that the formation of compound (III) in step a) is performed at 0~120° C.

5. The process according to claim 1, characterized in that the formation of compound (IV) in step b) is performed in the presence of a solvent, wherein the solvent is selected from the group consisting of DCM, THE, ACN and Acetone.

6. The process according to claim 5, characterized in that the volume of solvent is from 5 to 15 V.

7. The process according to claim 1, characterized in that the formation of compound (IV) in step b) is performed in the presence of an acid, wherein the acid is HCl.

8. The process according to claim 7, characterized in that the equivalent of acid is from 5 to 15 eq.

9. The process according to claim 1, characterized in that the formation of compound (IV) in step b) is performed at −20~70° C.

10. The process according to claim 1, characterized in that the formation of compound (I) in step c) is performed in the presence of a base, wherein the base is selected from the group consisting of $Na_2CO_3$, $K_2CO_3$, $NaHCO_3$, $KHCO_3$, NaOH, and KOH.

11. The process according to claim 1, characterized in that the formation of compound (I) in step c) is performed in the presence of an additive, wherein the additive is selected from the group consisting of $H_2O$, TEA, t-BuOH, IPA, PEG-400, TPGS-750-M, DMF, Glycerol and DMAc.

12. The process according to claim 1, characterized in that the formation of compound (I) in step c) is performed in the presence of a solvent, wherein the solvent is selected from the group consisting of IPAc, EtOAc, MTBE, Tol, THE, 2-MeTHF and TAAz.

13. The process according to claim 1, characterized in that the formation of compound (I) in step c) is performed in the presence of a catalyst, wherein the catalyst is selected from the group consisting of $Pd(OAc)_2$ and $Pd_2(dba)_3$.

14. The process according to claim 1, characterized in that the formation of compound (I) in step c) is performed in the presence of a ligand, wherein the ligand is selected from the group consisting of BrettPhos, AdCyBrettPhos, tBuBrettPhos, AdBrettPhos, RocPhos, tBuXphos, BippyPhos, MetBuXphos and $Me_3MeOtBuXphos$.

15. The process according to claim 1, characterized in that the formation of compound (I) in step c) is performed at 20~102° C. for 1~16 hours.

16. The process according to claim 1, characterized in that the formation of compound (I) in step c) further comprising recrystallization in a solvent, wherein the solvent is selected from the group consisting of heptane, hexane and petroleum ether.

17. The process according to claim 16, characterized in that the recrystallization is performed at 20~80° C. for 1~48 hours.

18. The process according to claim 1, characterized in that the formation of compound (I) in step c) further comprising removing residual Pd after the cross coupling reaction using metal scavengers, wherein the metal scavengers are selected from the group consisting of one or more of SiliaMetS Thiol, SiliaMetS DMT, SiliaBond Amine, SiliaMetS AMPA, SiliaMetS Cysteine, SiliaMetS DEAM, SiliaMetS Diamine, SiliaMetS DOTA, SiliaMetS Imidazole, SiliaMetS TAAcOH, SiliaMetS TAACONa, SiliaMetS Thiourea, SiliaBond Tosic Acid, SiliaMetS Triamine and MP-TMT.

* * * * *